United States Patent [19]

Wang

[11] Patent Number: 5,488,173

[45] Date of Patent: Jan. 30, 1996

[54] PROCESS FOR SELECTIVE ORTHO-METHYLATION OF CYCLOHEXANONES IN THE VAPOR PHASE

[76] Inventor: Fey-Long Wang, Department of Applied Chemistry, Providence University, Sha-Lu, Taichung Hsien, 43301, Taiwan

[21] Appl. No.: 285,152

[22] Filed: Aug. 3, 1994

[51] Int. Cl.[6] ..................................................... C07C 45/68
[52] U.S. Cl. ........................ 568/347; 568/804; 568/799
[58] Field of Search .................................... 568/799, 804, 568/391, 347

[56] References Cited

U.S. PATENT DOCUMENTS

| | | | |
|---|---|---|---|
| 2,549,520 | 4/1951 | Prichard | 568/347 |
| 3,932,518 | 1/1976 | Arpe | 568/347 |
| 4,201,880 | 5/1980 | van Sorge | 568/804 |
| 4,386,226 | 5/1983 | Adey et al. | 568/804 |
| 4,590,306 | 5/1986 | Korff et al. | 568/804 |
| 4,906,793 | 3/1990 | Callo et al. | 568/804 |
| 4,933,509 | 6/1990 | Warner | 563/804 |

*Primary Examiner*—James H. Reamer
*Attorney, Agent, or Firm*—Michael D. Bednarek; Marks & Murase

[57] ABSTRACT

A cyclohexanone having at least one ortho-hydrogen is selectively methylated in the ortho-position in the vapor phase. High conversion of the selected cyclohexanone and high selectivity in the ortho-position are obtained. The reaction products include 2-methylcyclohexanone, 2,6-dimethylcyclohexanone and 2,6-xylenol.

12 Claims, No Drawings

PROCESS FOR SELECTIVE ORTHO-METHYLATION OF CYCLOHEXANONES IN THE VAPOR PHASE

BACKGROUND OF THE INVENTION

1. Field of the Invention

The present invention relates to a process for selectively ortho-methylating a cyclohexanone having at least one ortho-hydrogen in the vapor phase, and more particularly to a methylation process of cyclohexanone for producing 2-methylcyclohexanone, 2,6-dimethylcyclohexanone and 2,6-xylenol.

2. Description of the Prior Art 2-methylcyclohexanone and 2,6-dimethylcyclohexanone are useful in chemical applications as intermediates. 2,6-xylenol is frequently used as a precursor to 2,3,6-trimethylphenol and other useful products. 2,6,-xylenol also finds uses in polymer and plastics applications such as that described in U.S. Pat. Nos. 3,446,856 and 3,994,982.

Currently, a process for the synthesis of 2,6-xylenol, which involves the vapor phase reaction of phenol with methanol in the presence of an acidic solid catalyst such as alumina, is in industrial use. However, in this process, the selectivity in the site of alkylation is only limited. That is, not only the ortho-positions of the phenolic nucleus but also the meta and para-positions thereof are subject to alkylation, so that a complicated procedure for the separation and purification of desired reaction products is required.

Another industrial process for the ortho-alkylation of phenol is based on the vapor phase reaction in the presence of magnesium oxide catalyst. However, this catalyst requires high temperature of 475° C. or higher, practically 500° C. or higher to achieve sufficient reaction. Moreover, its activity tends to become lower after a short period time of reaction.

In order to solve these problems, there have been proposed a number of catalysts including, for example, combinations of magnesium oxide and other oxides, combinations of iron oxide and other oxides, and the like. However, owing to the effect of the delocalized π electronic cloud of the benzene ring in phenol, these catalysts still have the disadvantages that they are insufficient in selectivity for ortho-alkylation and the service life of them are not desirably long. In addition, many undesirable by-products such as 2,4,6-trialkylphenol are formed.

SUMMARY OF THE INVENTION

It is therefore an object of this invention to provide a process for selectively ortho-methylating a cyclohexanone having at least one ortho-hydrogen in the vapor phase.

Another object of this invention is to provide a process for selectively ortho-methylating cyclohexanone in the vapor phase.

A further object of this invention is to provide a methylation process for producing 2-methylcyclohexanone and 2,6-dimethylcyclohexanone.

A further object of this invention is to provide a methylation process for producing 2,6-xylenol.

A still further object of this invention is to provide a methylation process for selectively ortho-methylating a cyclohexanone in the vapor phase with a high degree of conversion of the selected cyclohexanone and with a high degree of selectivity in the ortho-position.

To achieve the above object, the process for selectively methylating a cyclohexanone in the ortho-position includes: reacting methanol with a cyclohexanone in the vapor phase in the presence of a metal oxide catalyst, wherein the cyclohexanone has the general formula

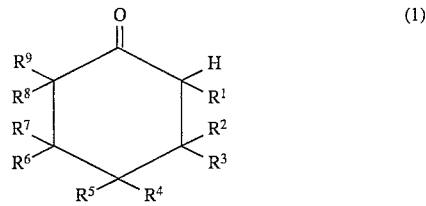

(1)

wherein each of $R^1$, $R^2$, $R^3$, $R^4$, $R^5$, $R^6$, $R^7$, $R^8$ and $R^9$ is selected from the group consisting of hydrogen, methyl, phenyl, and methyl-substituted phenyl.

DETAILED DESCRIPTION OF THE INVENTION

The cyclohexanone suitable for use in the present invention can be any cyclohexanone having at least one ortho-hydrogen, which has the general formula

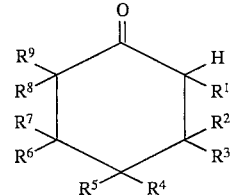

wherein each of $R^1$, $R^2$, $R^3$, $R^4$, $R^5$, $R^6$, $R^8$, and $R^9$ is selected from the group consisting of hydrogen, methyl, phenyl, and methyl-substituted phenyl.

Examples of such cyclohexanones include cyclohexanone, 2-methylcyclohexanone and 2,5-dimethylcyclohexanone. The catalyst suitable for use in the present invention can be any conventional metal oxide catalyst, such as titanium oxide, alumina, zirconium oxide, silicon oxide, magnesium oxide, zinc oxide, lead oxide, iron oxide and mixtures of any two or more of these.

The combination of $V/TiO_2$- (a metal oxide other than $TiO_2$) catalyst is a preferable example, wherein from 0 to 20% by weight of the catalyst, the molar ratio the metal to Ti is from 0 to 1. The metal oxide other than $TiO_2$ is also in the catalog of the above-mentioned conventional metal oxide catalysts.

Vanadium and any other metals used in the present invention may be obtained from any of their usual compounds such as nitrates hydroxides, carbonates oxalates, halides, and the like. They may be converted to the desired oxides by immersing, mixing, coprecipitation or other conventional methods.

In accordance with the process of the invention, a mixture of methanol and the selected cyclohexanone is vaporized and passed through a reactor containing the selected catalyst at an elevated temperature. One or both ortho-positions of the selected cyclohexanone will be methylated. Not only the ortho-methylated cyclohexanones are formed, but also the ortho-methylated phenols are formed.

The reaction temperature is typically in the range of from 250°–400° C., and the preferred range is from 300°–400° C.

The presence of an inert gas such as nitrogen, helium and argon is often helpful.

The reaction pressure is not critical. It may be carried out at atmospheric pressure, and may also be carried out over a wide range of pressure varying from about 0.5 to 10 atm.

In the case of cyclohexanone ($C_6H_{10}O$), that is, each of $R^1$, $R^2$, $R^3$, $R^4$, $R^5$, $R^6$, $R^7$, $R^8$ and $R^9$ in formula (1) is hydrogen, three major products, i.e., 2-methylcyclohexanone, 2,6-dimethylcyclohexanone and 2,6-xylenol, are formed. According to the examples of this invention described below, one who skilled in the art can optionally increase the yield of any desired product by adjusting the reaction condition.

In the examples, the following definitions apply, in which "CYH" indicates cyclohexanone:

$$\text{conversion}(\%) = \frac{\text{the CYH in feed} - \text{the unreacted CYH}}{\text{the CYH in feed}} \times 100\%$$

$$\text{selectivity}(\%) = \frac{\text{desired product}}{\text{the CYH in feed} - \text{the unreacted CYH}} \times 100\%$$

All in mole/hr.

The following specific examples are intended to demonstrate this invention more fully without acting as a limitation upon its scope, since numerous modifications and variations will be apparent to those skilled in the art.

EXAMPLE 1

Preparation of V/TiO$_2$ Catalyst

A catalyst containing 2.5% of vanadium by weight was prepared as follows. To 1 L of deionized water containing 2.47 g of oxalic acid ($H_2C_2O_4 \cdot 2H_2O$), 1.15 g of ammonium vanadate ($NH_4VO_3$) was dissolved yielding a blue solution. Then 20 g of a TiO$_2$ support was added to obtain a slurry. Impregnation took place as the slurry was stirred in a water bath at 100° C. to evaporate excess water. The resulting cake was dried at 110° C. in an oven overnight.

The obtained solid was ground and sieved to get 20–40 mesh size particles. The particles were finally calcined by slowly heating from room temperature to 500° C. at a heating rate of 10° C./min, and were holding for 6 hours at the final temperature of 500° C.

The above procedures were repeated to prepare a series of V/TiO$_2$ catalyst with different vanadium weight percentage, i.e., 0.1%, 1.0%, 5.0%, and 20.0%. The weight percentage of vanadium was controlled by the amount of oxalic acid and ammonium vanadate being added, however, the molar ratio of oxalic acid to ammonium vanadate was fixed to 2:1.

EXAMPLE 2

A mixture of methanol and cyclohexanone was fed by a syringe pump and vaporized in an evaporator. The vapor was adjusted to a constant rate of 15 mL/min and then was diluted with nitrogen. The diluted vapor contained 31% by volume of methanol and 3.1% of cyclohexanone, and the remainder was nitrogen. The diluted vapor was fed into a fixed-bed isothermal quartz reactor with an inside diameter of 1.8 cm at a total flow rate of 45 ml/min, in which the reactor was filled with 1 g of the V/TiO$_2$ catalyst (with various V contents) obtained form example 1. The reaction temperature was 350° C. The products were analyzed quantitatively with a chromatography attached to the reactor through a gas-sampling valve. The results according to different vanadium contents are shown in Table 1.

TABLE 1

Reactions of methanol and cyclohexanone in the presence of V/TiO$_2$ catalyst over various vanadium contents

| wt % of V (%) | conversion (%) | selectivity (%) | | |
|---|---|---|---|---|
| | | 2-methyl-cyclo-hexanone | 2,6-dimethyl-cyclohexanone | 2,6-xylenol |
| 0.1 | 26.0 | 23.6 | 7.7 | 1.6 |
| 1.0 | 50.8 | 46.9 | 21.4 | 2.9 |
| 2.5 | 69.3 | 37.7 | 46.8 | 4.9 |
| 5.0 | 86.7 | 15.7 | 52.1 | 27.2 |
| 20.0 | 88.6 | 12.1 | 53.5 | 32.5 |

EXAMPLE 3

The same procedures described in example 2 were employed, except that the vanadium content in the V/TiO$_2$ catalyst was fixed to 2.5 wt % and the reaction temperature was varied. The results according to different reaction temperatures are shown in Table 2.

TABLE 2

Reactions of methanol and cyclohexanone in the presence of V(2.5 wt %)/TiO$_2$ catalyst over various reaction temperatures

| temp (°C.) | conversion (%) | selectivity (%) | | |
|---|---|---|---|---|
| | | 2-methyl-cyclo-hexanone | 2,6-dimethyl-cyclohexanone | 2,6-xylenol |
| 300 | 24.9 | 5.7 | 12.48 | trace |
| 320 | 27.7 | 34.29 | 6.92 | 4.3 |
| 340 | 57.39 | 43.76 | 35.07 | 3.58 |
| 350 | 69.3 | 37.7 | 46.8 | 4.9 |
| 360 | 76.78 | 30.67 | 30.52 | 6.96 |
| 380 | 88.4 | 19.13 | 51.04 | 26.84 |
| 400 | 93.31 | 7.11 | 25.04 | 51.63 |

EXAMPLE 4

The same procedures described in example 2 were employed, except that the vanadium content in the V/TiO$_2$ catalyst was fixed to 2.5% and though the total feed composition of methanol plus cyclohexanone was also 34.1% by volume, the methanol to cyclohexanone ratio was varied. The results according to different methanol to cyclohexanone ratios by volume are shown in Table 3.

TABLE 3

Reactions of methanol and cyclohexanone in the presence of V(2.5 wt %)/TiO$_2$ catalyst over various methanol to cyclohexanone molar ratios

| molar ratio of methanol to cyclo-hexanone (%) | conversion (%) | selectivity (%) | | |
|---|---|---|---|---|
| | | 2-methyl-cyclo-hexanone | 2,6-dimethyl-cyclohexanone | 2,6-xylenol |
| 1.7 | 14.59 | 65.9 | 22.4 | trace |
| 3.3 | 39.31 | 56.3 | 29.4 | 6.9 |
| 9.7 | 71.22 | 37.1 | 52.2 | 8.8 |
| 14.8 | 94.56 | 12.8 | 69.5 | 16.5 |

TABLE 3-continued

Reactions of methanol and cyclohexanone in the presence of V(2.5 wt %)/TiO$_2$ catalyst over various methanol to cyclohexanone molar ratios

| molar ratio of methanol to cyclohexanone (%) | conversion (%) | selectivity (%) | | |
|---|---|---|---|---|
| | | 2-methyl-cyclohexanone | 2,6-dimethyl-cyclohexanone | 2,6-xylenol |
| 18.8 | 92.2 | 8.5 | 72.3 | 17.0 |
| 30.5 | 78.49 | 13.9 | 75.1 | 11.0 |
| 73.7 | 82.89 | 0.0 | 82.4 | 17.6 |

EXAMPLE 5

The same procedures described in example 2 were employed, except that the vanadium content in the V/TiO$_2$ catalyst was fixed to 2.5% and the amount of catalyst used was varied. The results according to different catalyst weights are shown in Table 4.

TABLE 4

Reactions of methanol and cyclohexanone in the presence of V(2.5 wt %)/TiO$_2$ catalyst over various catalyst weights

| catalyst weight (g) | conversion (%) | selectivity (%) | | |
|---|---|---|---|---|
| | | 2-methyl-cyclohexanone | 2,6-dimethyl-cyclohexanone | 2,6-xylenol |
| 0.3 | 42.1 | 45.1 | 21.7 | 2.57 |
| 0.5 | 55 | 32.8 | 25.9 | 10.8 |
| 1 | 69.3 | 37.7 | 46.8 | 4.9 |
| 2 | 87.1 | 21.9 | 48.5 | 18.3 |
| 4 | 100 | 0.9 | 42.3 | 41.9 |

EXAMPLE 6

Preparation of TiO$_2$—Al$_2$O$_3$ Catalyst 1 mole of aluminum chloride (AlCl$_3$) was added into 1 L of cool deionized water containing a mole of titanium tetrachloride (TlCl$_4$) to form a solution. The solution was stirred at 100° C. in a water bath and excess urea was added to make coprecipitation occurred. The resulting cake was dried at 110° C. in an oven overnight.

The obtained solid was ground and sieved to get 20–40 mesh size particles. The particles were finally calcined by slowly heating from room temperature to 500° C. at a heating rate of 10° C./min, and were holding for 6 hours at the final temperature of 500° C.

EXAMPLE 7

Preparation of TiO$_2$—ZrO$_2$ Catalyst

The same procedures described in example 6 were employed, except that aluminum chloride was replaced by zirconium chloride (ZrCl$_3$).

EXAMPLE 8

Preparation of TiO$_2$—SiO$_2$ Catalyst

The same procedures described in example 6 were employed, except that aluminum chloride was replaced by sodium silicate (NaSiO$_2$). TiO$_2$—SiO$_2$ catalysts with other Ti to Si molar ratios were also prepared, i.e., Ti/Si=2,4 and 8.

EXAMPLE 9

The same procedures described in example 2 were employed, except that the reactor was filled with 1 g of the TiO$_2$—Al$_2$O$_3$, TiO$_2$—ZrO$_2$, or TiO$_2$—SiO$_2$ catalyst obtained from example 6, 7, or 8 respectively. The results are shown in Table 5.

TABLE 5

Reactions of methanol and cyclohexanone over various catalysts

| catalyst | conversion (%) | selectivity (%) | | |
|---|---|---|---|---|
| | | 2-methyl-cyclohexanone | 2,6-dimethyl-cyclohexanone | 2,6-xylenol |
| TiO$_2$—Al$_2$O$_3$ (Ti/Al = 1) | 95.7 | 7.4 | 3.4 | 20.4 |
| TiO$_2$—ZrO$_2$ (Ti/Zr = 1) | 82.4 | 23.3 | 10.8 | 8.8 |
| TiO$_2$—SiO$_2$ (Ti/Si = 1) | 76.7 | 10.2 | 27.5 | 3.5 |
| TiO$_2$—SiO$_2$ (Ti/Si = 2) | 81.6 | 7.4 | 17.1 | 14.6 |
| TiO$_2$—SiO$_2$ (Ti/Si = 4) | 96.4 | 23.7 | 26.9 | 17.4 |
| TiO$_2$—SiO$_2$ (Ti/Si = 8) | 98.2 | 10.2 | 7.8 | 11.2 |

EXAMPLE 10

Preparation of V(8 wt %)/TiO$_2$—SiO$_2$ Catalyst

A V/TiO$_2$—SiO$_2$ catalyst containing 8% of vanadium by weight was prepared as follows. To 1 L of deionized water containing 7.91 g of oxalic acid, 3.68 g of ammonium vanadate was dissolved yielding a blue solution. Then 20 g of the TiO$_2$—SiO$_2$ support (with various Ti/Si ratios) prepared from example 8 was added to obtain a slurry. Impregnation took place as the slurry was stirred in a water bath at 100° C. to evaporate excess water. The resulting cake was dried at 110° C. in an oven overnight.

The obtained solid was ground and sieved to get 20–40 mesh size particles. The particles were finally calcined by slowly heating from room temperature to 500° C. at a heating rate of 10° C./min, and were holding for 6 hours at the final temperature of 500° C.

EXAMPLE 11

The same procedures described in example 2 were employed, except that the reactor was filled with 1 g of V(8 wt %)/TiO$_2$—SiO$_2$ catalyst (with various Ti/Si ratios) obtained from example 10. The results are shown in Table 6.

TABLE 6

Reactions of methanol and cyclohexanone in the presence of V(8 wt %)/TiO$_2$—SiO$_2$ catalyst over various Ti/Si molar ratios

| Ti/Si molar ratio | conversion (%) | selectivity (%) | | |
|---|---|---|---|---|
| | | 2-methyl-cyclo-hexanone | 2,6-dimethyl-cyclohexanone | 2,6-xylenol |
| 1/1 | 90.9 | 16.6 | 22.9 | 6.0 |
| 2/1 | 84.5 | 15.6 | 4.7 | 6.3 |
| 4/1 | 91.7 | 8.7 | 25.4 | 18.0 |
| 8/1 | 95.3 | 7.8 | 35.3 | 12.9 |

Example 12: Preparation of V/TiO$_2$—SiO$_2$ (Ti/Si=4) catalyst The procedures described in example 1 were employed, except that the TiO$_2$—SiO$_2$(Ti/Si=4) support prepared from example 8 was used in place of the TiO$_2$ support. TiO$_2$SiO$_2$(Ti/Si=4) catalysts containing various vanadium contents were also prepared, i.e., 0, 2.5, 5.0, 12.0, 16.0 wt % of vanadium.

EXAMPLE 13

The same procedures described in example 2 were employed, except that the reactor was filled with V/TiO$_2$—SiO$_2$ (Ti/Si=4) catalyst prepared from example 12 and the vanadium content was varied. The results according to different vanadium contents are shown in Table 7.

TABLE 7

Reactions of methanol and cyclohexanone in the presence of V/TiO$_2$—SiO$_2$ (Ti/Si = 4) catalyst over various vanadium contents

| wt % of V (%) | conversion (%) | selectivity (%) | | |
|---|---|---|---|---|
| | | 2-methyl-cyclo-hexanone | 2,6-dimethyl-cyclohexanone | 2,6-xylenol |
| 0 | 93.5 | 8.3 | 6.3 | 37.4 |
| 2.5 | 98.4 | 5.9 | 6.2 | 44.9 |
| 5.0 | 98.1 | 2.7 | 3.9 | 43.2 |
| 8.0 | 98.9 | 1.1 | 5.5 | 50.4 |
| 12.0 | 98.8 | 1.4 | 9.0 | 53.8 |
| 16.0 | 98.9 | 3.7 | 9.4 | 43.6 |

EXAMPLE 14

The same procedures described in example 13 were employed, except that the vanadium content in the V/TiO$_2$—SiO$_2$ (Ti/Si=4) catalyst was fixed to 12% and the reaction temperature was varied. The results according to different reaction temperatures are shown in Table 8.

TABLE 8

Reactions of methanol and cyclohexanone in the presence of V(12 wt %)/TiO$_2$—SiO$_2$ (Ti/Si = 4) catalyst over various reaction temperatures

| temp (°C.) | conversion (%) | selectivity (%) | | |
|---|---|---|---|---|
| | | 2-methyl-cyclo-hexanone | 2,6-dimethyl-cyclohexanone | 2,6-xylenol |
| 250 | 78.9 | 21.4 | 7.2 | 1.4 |
| 270 | 82.5 | 29.4 | 25.6 | 2.9 |
| 310 | 85.6 | 3.5 | 22.5 | 13.2 |
| 330 | 93.3 | 2.4 | 12.8 | 29.2 |
| 350 | 98.8 | 1.4 | 9.0 | 53.8 |
| 360 | 99.8 | 2.5 | 7.0 | 47.6 |

EXAMPLE 15

The same procedures described in example 13 were employed, except that the vanadium content in the V/TiO$_2$—SiO$_2$ (Ti/Si=4) catalyst was fixed to 12% and though the total feed composition of methanol plus cyclohexanone was also 34.1% by volume, the methanol to cyclohexanone ratio was varied. The results according to different methanol to cyclohexanone ratios by volume are shown in Table 9.

TABLE 9

Reactions of methanol and cyclohexanone in the presence of V(12 wt %)/TiO$_2$—SiO$_2$ (Ti/Si = 4) catalyst over various methanol to cyclohexanone ratios

| molar ratio of methanol to cyclo-hexanone | conversion (%) | selectivity (%) | | |
|---|---|---|---|---|
| | | 2-methyl-cyclo-hexanone | 2,6-dimethyl-cyclohexanone | 2,6-xylenol |
| 15 | 98.2 | 4.4 | 6.7 | 36.1 |
| 12 | 100 | 2.2 | 13.4 | 42.2 |
| 10 | 98.8 | 1.4 | 9.0 | 53.8 |
| 7 | 90.5 | 12.9 | 15.5 | 23.7 |
| 4 | 83.7 | 12.9 | 9.5 | 28.7 |
| 2 | 84.7 | 20.9 | 8.0 | 26.4 |

EXAMPLE 16

The same procedures described in example 13 were employed, except that the vanadium content in the V/TiO$_2$—SiO$_2$ (Ti/Si=4) catalyst was fixed to 12% and the amount of catalyst used was varied. The results according to different catalyst weights are shown in Table 10.

TABLE 10

Reactions of methanol and cyclohexanone in the present of V(12 wt %)/TiO$_2$—SiO$_2$ (Ti/Si = 4) catalyst over various catalyst weights

| catalyst weight (g) | conversion (%) | selectivity (%) | | |
|---|---|---|---|---|
| | | 2-methyl-cyclo-hexanone | 2,6-dimethyl-cyclohexanone | 2,6-xylenol |
| 0.3 | 85.2 | 2.4 | 16.2 | 50.1 |
| 0.5 | 92.4 | 1.8 | 12.0 | 48.9 |
| 1 | 98.8 | 1.4 | 9.0 | 53.8 |
| 1.5 | 98.2 | 2.2 | 7.0 | 50.2 |
| 2 | 98.0 | 2.3 | 7.2 | 50.1 |

EXAMPLE 17

The same procedures described in example 2 were employed, except that 2-methylcyclohexanone was substituted for cyclohexanone, and the reactor was filled with 1 g of the V(12 wt %)/TiO$_2$—SiO$_2$(Ti/Si=4) catalyst prepared from example 12. The results are that conversion(%) of 2-methylcyclohexanone is 52%, selectivity to 2,6-dimethylcyclohexanone is 9% and selectivity to 2,6-xylenol is 12%.

What is claimed is:

1. A process for selectively methylating a cyclohexanone in the ortho-position to produce orthomethylated cyclohexanones and ortho-methylated phenols, which comprises reacting methanol with the cyclohexanone in the vapor phase in the presence of a metal oxide catalyst, wherein the cyclohexanone has the general formula

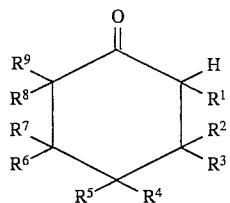

wherein $R^1$, is one member selected from the group consisting of hydrogen and methyl, wherein $R^2$, $R^3$, $R^4$, $R^5$, $R^6$, $R^7$, $R^8$, and $R^9$ each are hydrogen and wherein the metal oxide catalyst is at least one member selected from the group consisting of titanium oxide, alumina, zirconium oxide, silicon oxide, magnesium oxide, zinc oxide, lead oxide, and iron oxide.

2. The process as claimed in claim 1, wherein $R^1$, is hydrogen and wherein the products of methylation comprise 2-methylcyclohexanone, 2,6-dimethylcyclohexanone, and 2.6-xylenol.

3. The process as claimed in claim 1, wherein $R^1$ is methyl, and wherein the products of methylation comprise 2,6-dimethylcyclohexanone and 2,6-xylenol.

4. The process as claimed in claim 1, wherein the metal oxide catalyst further comprises vanadium.

5. The process as claimed in claim 4, wherein the metal oxide catalyst contains from 0 to 20% by weight of vanadium.

6. The process as claimed in claim 4, wherein the metal oxide catalyst comprises two or more compounds selected from the group consisting of titanium oxide, alumina, zirconium oxide, silicon oxide, magnesium oxide, zinc oxide, lead oxide, and iron oxide, one compound of which is titanium oxide, and the molar ratio of the metal in the compound which is not titanium oxide to Ti is from 0 to 1.

7. The process as claimed in claim 4, wherein the compound which is not titanium oxide is at least one member selected from the group consisting of alumina, zirconium oxide, silicon oxide, magnesium oxide, zinc oxide, lead oxide, and iron oxide.

8. The process as claimed in claim 7, wherein the the compound which is not titanium oxide is alumina.

9. The process as claimed in claim 7, wherein the the compound which is not titanium oxide is zirconium oxide.

10. The process as claimed in claim 7, wherein the the compound which is not titanium oxide is silicon oxide.

11. The process as claimed in claim 1, wherein the methylation is carried out at a temperature in the range of 300°–400° C.

12. The process as claimed in claim 1, wherein the molar ratio of methanol to the cyclohexanone is greater than 1.

* * * * *